United States Patent
Breivik et al.

(10) Patent No.: US 11,992,474 B2
(45) Date of Patent: May 28, 2024

(54) COMPOSITION FOR TREATMENT OF DRY EYE DISEASE AND MEIBOMIANITIS

(71) Applicant: Epax Norway AS, Ålesund (NO)

(72) Inventors: Harald Breivik, Inndyr (NO); Harald Svensen, Ålesund (NO); Iren Merete Skjåstad Stoknes, Ålesund (NO)

(73) Assignee: EPAX NORWAY AS, Ålesund (NO)

(*) Notice: Subject to any disclaimer, the term of this patent is extended or adjusted under 35 U.S.C. 154(b) by 750 days.

(21) Appl. No.: 16/973,852

(22) PCT Filed: Jun. 19, 2019

(86) PCT No.: PCT/NO2019/050128
§ 371 (c)(1),
(2) Date: Dec. 10, 2020

(87) PCT Pub. No.: WO2019/245382
PCT Pub. Date: Dec. 26, 2019

(65) Prior Publication Data
US 2021/0361606 A1    Nov. 25, 2021

(30) Foreign Application Priority Data
Jun. 19, 2018 (NO) .................................. 20180849

(51) Int. Cl.
*A61K 31/202* (2006.01)
*A23L 33/12* (2016.01)
(Continued)

(52) U.S. Cl.
CPC ............ *A61K 31/202* (2013.01); *A23L 33/12* (2016.08); *A61K 35/60* (2013.01); *A61P 27/04* (2018.01)

(58) Field of Classification Search
CPC ....... A61K 31/202; A61K 35/60; A23L 33/12; A61P 27/04; A61P 27/02
See application file for complete search history.

(56) References Cited

U.S. PATENT DOCUMENTS

| 8,021,874 B2 | 9/2011 | Anderson et al. |
| 8,957,110 B2 | 2/2015 | Aleo et al. |

(Continued)

FOREIGN PATENT DOCUMENTS

| WO | 2004/006801 | 1/2004 |
| WO | 2006/007510 | 1/2006 |

(Continued)

OTHER PUBLICATIONS

Taka Yuki, Sassa et al., "Very long-chain tear film lipids produced by fatty acid elongase ELOVL1 prevent dry eye disease in mice", FASEB J. 2018, 32(6). pp. 2966-2978, Epub Jan. 17, 2018, (Year: 2018).*

(Continued)

*Primary Examiner* — Deborah D Carr
(74) *Attorney, Agent, or Firm* — Wenderoth, Lind & Ponack, L.L.P.

(57) ABSTRACT

The present application relates to compositions for treatment of eye disorders, particularly for treatment of dry eye disease (DED) and meibomianitis, wherein the composition comprises very long chain polyunsaturated fatty acids. Further, the invention provides a method for treatment of DED and meibomianitis of a subject, comprising administering to the subject a composition comprising very long chain polyunsaturated fatty acids derived from natural oils. The compositions for use are suitable for oral and local applications.

21 Claims, 3 Drawing Sheets

(51) Int. Cl.
*A61K 35/60* (2006.01)
*A61P 27/04* (2006.01)

(56) References Cited

U.S. PATENT DOCUMENTS

| | | | | |
|---|---|---|---|---|
| 2007/0265341 | A1* | 11/2007 | Dana | C12Q 1/68 |
| | | | | 435/6.16 |
| 2008/0153909 | A1 | 6/2008 | Dana et al. | |
| 2009/0118243 | A1 | 5/2009 | Gjorstrup | |
| 2009/0203787 | A1 | 8/2009 | Anderson et al. | |
| 2012/0010280 | A1 | 1/2012 | Aleo et al. | |
| 2012/0071558 | A1 | 3/2012 | Anderson et al. | |
| 2013/0005691 | A1 | 1/2013 | Gallois-Bernos | |
| 2013/0190399 | A1* | 7/2013 | Raman | C07C 67/343 |
| | | | | 554/224 |
| 2014/0100280 | A1 | 4/2014 | Anderson et al. | |
| 2018/0044278 | A1 | 2/2018 | Bazan et al. | |

FOREIGN PATENT DOCUMENTS

| | | | | |
|---|---|---|---|---|
| WO | 2009/051670 | | 4/2009 | |
| WO | WO-2009051670 A2 * | | 4/2009 | ........... A61K 31/202 |
| WO | 2009/097331 | | 8/2009 | |
| WO | 2010/010365 | | 1/2010 | |
| WO | 2010/106571 | | 9/2010 | |
| WO | WO-2010106571 A2 * | | 9/2010 | ............ A61K 31/20 |
| WO | 2011/053892 | | 5/2011 | |
| WO | WO-2011053892 A1 * | | 5/2011 | ........... C07C 29/103 |
| WO | 2013/091020 | | 6/2013 | |
| WO | 2013/170006 | | 11/2013 | |
| WO | 2016/130522 | | 8/2016 | |
| WO | 2016/182452 | | 11/2016 | |
| WO | 2018/175288 | | 9/2018 | |

OTHER PUBLICATIONS

International Search Report (ISR) dated Sep. 13, 2019 in International (PCT) Application No. PCT/NO2019/050128.
Norwegian Search Report dated Nov. 30, 2018 in corresponding Norwegian Application No. 20180849.
Hideko Tanaka et al., "Association between very long chain fatty acids in the meibomian gland and dry eye resulting from n-3 fatty acid deficiency", Prostaglandins, Leukotrienes and Essential Fatty Acids, vol. 97, pp. 1-6 (2015).
Akiko Harauma et al., "Potential for daily supplementation of n-3 fatty acids to reverse symptoms of dry eye in mice", Prostaglandins, Leukotrienes and Essential Fatty Acids, vol. 90, pp. 207-213 (2014).

* cited by examiner

COMPOSITION FOR TREATMENT OF DRY EYE DISEASE AND MEIBOMIANITIS

FIELD OF THE INVENTION

The present invention relates to compositions for treatment of eye disorders, particularly for alleviation of symptoms of dry eye disease (DED) and meibomianitis, wherein the composition comprises very long chain polyunsaturated fatty acids. Further, the invention provides a method for treatment of DED and meibomianitis of a subject, comprising administering to the subject a composition comprising very long chain polyunsaturated fatty acids derived from natural oils. The compositions for use are for oral and local applications.

BACKGROUND OF THE INVENTION

Among the long-chain polyunsaturated fatty acids (LCPUFAs), and especially long-chain omega-3 fatty acids (LCn3), the fatty acids of chain length C20-C22 have received most interest in literature. The acronyms EPA (for eicosapentaenoic acid) and DHA (for docosahexaenoic acid) have become household names in describing valuable omega-3-acids from fish oil and other sources. Products rich in alpha-linoleic acid (ALA) from plant sources are also available in the market. In this regard, it is noted that lipids are described by the formula X:YnZ wherein X is the number of carbon atoms in their alkyl chain, and Y is the number of double bonds in such chain; and where "nZ" is the number of carbon atoms from the methyl end group to the first double bond. In nature the double bonds are all in the cis-form. In polyunsaturated fatty acids each double bond is separated from the next by one methylene ($-CH_2$) group. Using this nomenclature, EPA is 20:5n3; DHA is 22:6n3 and ALA is C18:3n3. Further, natural sources of omega-3 fatty acids, such as fish oil, also comprise fatty acids of shorter and longer length than C20-C22. As is employed herein, very long chain fatty acids (or VLCFAs) is intended to mean fatty acids (or FAs) having a chain length of more than 22 carbon atoms; the term very long chain polyunsaturated fatty acids (or VLCPUFAs) is intended to mean polyunsaturated fatty acids (or PUFAs) having a chain length of more than 22 carbon atoms; the term very long chain monounsaturated fatty acids (or VLCMUFAs) is intended to mean monounsaturated fatty acids (or MUFAs) having a chain length of more than 22 carbon atoms; while the term VLCn3 is intended to refer to polyunsaturated omega-3 fatty acids having a chain length of more than 22 carbon atoms, it being understood that VLCn3 represents a sub-group of VLCPUFA. Further, as is employed herein, the term very long chain unsaturated fatty acids (or VLCUSFAs) is intended to mean unsaturated fatty acids, mono- or poly-, having a chain length of more than 22 carbon atoms. The term very long chain saturated fatty acids (VLCSFAs) is intended to mean saturated fatty acids, having a chain length of more than 22 carbon atoms.

In order to produce marine omega-3-concentrates rich in EPA and DHA, conventional industrial processes are designed to concentrate the C20-C22 fraction, by removing both short-chain fatty acids as well as larger molecules than the C22 fatty acids. Examples of such processes are molecular/short path distillation, urea fractionation, extraction and chromatographic procedures, all of which can be utilized to concentrate the C20-22 fraction of marine fatty acids and similar materials derived from other sources. A review of these procedures is provided in Breivik H (2007) Concentrates. In: Breivik H (ed) Long-Chain Omega-3 Specialty Oils. The Oily Press, P J Barnes & Associates, Bridgwater, UK, pp 111-140.

Omega-3-acids are very liable to oxidation. In order to comply with pharmacopoeia and voluntary standards imposing upper limits for oligomeric/polymeric oxidation products, it is common to remove components with chain length above that of DHA, for example by distillation, extraction and similar procedures. Further, such higher molecular weight components of marine oils are typically associated with undesirable unsaponifiable constituents of such oil including cholesterol as well as with organic pollutants such as brominated diphenyl ethers.

Omega-3 fatty acids, and particularly the LCPUFAs EPA and DHA, are known to have a broad range of beneficial health effects and are hence known for different uses. It is also known to use these fatty acids in treatment of eye disorders and diseases.

Dry eye disease (DED), also known as keratoconjunctivitis sicca (KCS), is a common chronic condition that is characterised by ocular discomforts and visual disturbances that decrease quality of life. As recently described by the Dry Eye Assessment and Management (DREAM) Study Research Group (New England Journal of Medicine, Apr. 13, 2018, DOI: 10.1056/NEJMoa1709691), many clinicians recommend the use of omega-3 fatty acids to relieve symptoms of DED. However, the large DREAM Study concluded that among patients with DED, those who received supplements as omega-3 concentrates (daily intake of 3000 mg n3 fatty acids as 2000 mg EPA and 1000 mg DHA in triglyceride form) for 12 months did not have significantly better outcomes than those who received placebo.

In contrast to this, other studies have shown positive effects on DED from fish oil. As an example, in an article listed among the references in the DREAM Study report, Deinema et al. (A randomized, double-masked, placebo controlled clinical trial of two forms of omega-3 supplements for treating dry eye disease. Ophthalmology 2017; 124: 43-52) showed significantly positive effects on DED by using non-concentrated fish oil and krill oil as omega-3 sources.

The DREAM study states that many clinicians recommend dietary supplements of omega-3 fatty acids because they have anti-inflammatory activity and are not associated with substantial side effects.

The dry eye disease (DED) is often related to meibomian gland dysfunction (MGD), also named meibomianitis. The meibomian glands are arranged inside the eyelid, around 30 glands on the upper lid margin and about 25 on the lower lid margin of each eye. These glands secrete an oil (Meibum) that protects the eyes, among other actions by creating a seal when the eyes are closed, and by interacting with the tear film, enhancing the tears by spreading them evenly and maintaining a consistent quality of vision, and by covering the tear film thereby slowing the rate of tear evaporation.

MGD can lead to altered tear film composition, ocular surface disease, ocular and eyelid discomfort, and evaporative dry eye (Chhadava P, Goldhardt R and Galor A (2017) meibomian Gland Disease. The role of gland dysfunction in Dry Eye Disease. Ophtalomology 124 (11) Supplement, S20-S26). Ageing is a known risk factor for MDG, as is environmental stress; it is suggested that both aging and environmental stress lead to depletion of meibocyte stem cells. Hormones affect meibocytes: MDG has been described in androgen-depleted states including persons on anti-androgen agents (treatment of benign prostatic hypertrophy, prostate cancer), individuals with complete androgen insensitivity syndrome, Sjögren syndrome. Medication by 13-cis-retenoid acid (Accutane, Hoffmann-La Roche) is associated with meibum hyposecretion, leading to DED symptoms. Topical medications, including topical epinephrine and topical glaucoma medications (e.g. topical β-blockers, prostaglandin analogues, carbonic anhydrase inhibitors) are associated with negative canges to the meibomian glands. Commensal bacteria such as *Staphylococcus aureus* can have negative effects on the composition of meibum. The use of contact lenses is associated with reduced meibomian gland function. Meibomian glands can also be decreased from birth. Chhadava et al. points to oral intake of omega-3 fatty acids as being associated with alternations in the polar lipid profile and decrease in the saturated fatty acid content of meibomian gland secretions and decrease of ocular surface inflammation in patients with DED and decrease of inflammatory lipid mediator profiles in tears. Flaxseed oil, fish oil and olive oil are mentioned as foods potentially rich in omega-3 acids; also supplementation with DHA is mentioned as might prove beneficial.

A review by Macsai (MS Macsai (2008) The role of omega-3 dietary supplementation in blepharitis and meibomian gland dysfunction (an AOS thesis) Trans Am Ophthalmol Soc. 2008; 106: 336-356) states that it is the ratio of omega-6 to omega-3 fatty acids that is important in influencing the overall inflammatory state of the body. Omega-3 FAs modulate prostaglandin metabolism toward anti-inflammatory prostaglandin synthesis. As blepharitis, MGD and dry eye are thought to be inflammatory diseases, a reduction in the systemic inflammatory state may alleviate blepharitis, MGD and dry eye-associated discomforts. In an accompanying figure for explaining the competing inflammatory and anti-inflammatory effects of omega-6 and omega-3 FAs the author shows the effects of omega-6 acids with chain length up to C20 (arachidonic acid) and omega-3 acids with chain length up to C22 (DHA). As an additional hypothesis the author states that supplementing with high amounts of omega-3 FAs is likely to change the FA composition in the meibomian gland, and that this change may be beneficial in tear stabilization and may prevent inflammation from blocking the meibomian gland ducts. Macsai's hypotheses regarding the effects of omega-3 FAs for alleviating MGD and dry eye-associated discomforts are also referred to in more recent publications.

U.S. Pat. No. 9,381,183 B2 (Smith et al.) teaches elevating the so-called omega-3 index in patients suffering from DED and MGD so as to facilitate the increase of omega-3 acids acting as an anti-inflammatory and, and at the same time decrease the amount of omega-6 acid. Smith et al. utilise supplementation of omega-3 fatty acids in re-esterified triglyceride form in order to provide a sufficient amount of omega-3 acids. The person skilled in the art will realise that this supplement description refers to omega-3 acids concentrated from fish oil in a similar manner as the material that was utilised in the DREAM Study. Rather similar to the amounts of omega-3 acid that was utilised in the DREAM Study, Smith et al. teaches the use of a daily dose of omega-3 fatty acids between 2000 and 3000 mg, comprising an effective amount of EPA (1600-2500 mg) and DHA (500-900 mg). Smith et al. refers to the so-called HS Omega-3 Index. The HS-Omega-3 Index test measures levels of the omega-3 fatty acids EPA and DHA in dried blood spots. The tables and other information that are disclosed by Smith et al., based on the HS-Omega-3 Index, relate to the content of the omega-3 acids EPA and DHA, omega-3 acids with chain length C20 and C22, respectively.

A very recent publication evaluates suitable methods for exploring the fatty acid status and clinically health outcomes (Harris W S (2018) The Omega-6:Omega-3 ratio: a critical appraisal and possible successor, Prostaglandins, Leukotrienes and Essential Fatty Acids 132: 34-40). The abstract recommends "a newer metric that focuses on the primary deficiency in Western diets—the lack of eicopsapentaenoic acid (EPA and DHA). The Omega-3 Index (red blood cell EPA+DHA) has much to recommend in this regard." The Omega-3 index, i.e. the measurement of EPA plus DHA, was chosen for a survey in 2016 to express worldwide omega-3 status, and by Health Canada for that country's national health survey. The single largest dataset published on circulating FA status in humans, which included about 160,000 individuals in the USA, utilised the Omega-3 Index. The Omega-3 Index has been used in multiple observational cohort and interventional studies around the world. It has been associated with lower risk for coronary disease sudden cardiac death, acute coronary syndromes, all-cause mortality and other health conditions such as impaired cognitive function, depression, aggressive behaviours and bipolar disease. The Omega-3 Index was the first omega-3 status test to achieve widespread use in clinical medicine in the US. The conclusion states: "The Omega-3-Index, a metric born in 2004 that fulfils many of the criteria of a bona fide risk factor, may be the marker of choice for the 21st century."

The above references illustrate that the scientific community acknowledges that the concentration of C20-C22 omega-3 acids, particularly EPA and DHA, represents a measure for the combined beneficial effects of the omega-3 fatty acids.

From the above references we see that intake of C20-C22 omega-3 fatty acids (EPA and DHA) are recommended by clinicians and widely used by patients to alleviate symptoms of DED, in addition to the sum of EPA plus DHA being assessed as representing the effect of all healthy omega-3 acids in the human body. The reason for the assumed positive effects of EPA and DHA on DED has been cited are due to the anti-inflammatory activity of these fatty acids; that these fatty acids are not associated with substantial side effects; that polyunsaturated fatty acids result in a less viscous meibum that flows better; by elevating the so-called omega-3 index in patients suffering from DED so as to facilitate the increase of the omega-3 acids EPA and DHA and decrease the (relative) amount of omega-6 acid. Very unfortunately, however, the large DREAM study, as cited above, concluded that those who received concentrates of the omega-3 acids EPA and DHA for 12 months did not have significantly better outcomes than the patients who received placebo.

Based on the above, there is a need for new and alternative methods and compositions for treatment of DED and meibomianitis patients, particularly to alleviate their symptoms associated with the disease.

BRIEF SUMMARY OF THE INVENTION

It is therefore an object of the present invention to provide a composition which is useful in the treatment of dry eye disease and meibomianitis and symptoms and conditions associated therewith. The present disclosure provides compositions for use in treatment of eye disorders, wherein the compositions comprise very long chain polyunsaturated fatty acids (VLCPUFA). In a first aspect, the invention provides a composition comprising very long chain polyunsaturated fatty acids derived from natural oils for treatment of Dry Eye Disease (DED) and meibomianitis. The compositions of the invention comprise an enriched amount of very long chain unsaturated fatty acids (VLCUSFAs). Particularly, the compositions comprise an enriched amount of both very long chain monounsaturated fatty acids (VLC-MUFAs) and very long chain polyunsaturated fatty acids (VLCPUFAs).

In an equal aspect, the invention provides a method for treatment of DED and meibomianitis of a subject, comprising administering to the subject a composition comprising VLCPUFAs derived from natural oils. The method comprises administering to the subject a therapeutically effective amount of the composition comprising VLCPUFA.

DETAILED DESCRIPTION OF THE INVENTION

Figure 1:
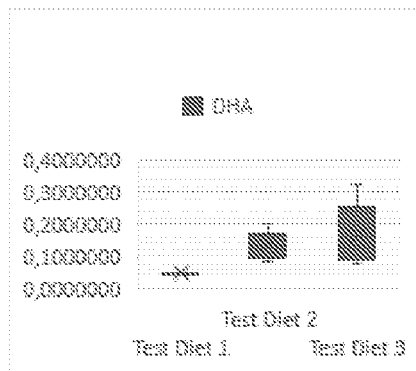
FIGS. 1 to 9 provide the content of different fatty acids in meibum tissue from mice fed different test diets.

Biologically active PUFAS, including omega-3 fatty acids, are not limited to the long chain fatty acids such as EPA and DHA. Breivik and Svensen in WO2016/182452 disclose a method for producing compositions of very long chain polyunsaturated fatty acids (VLCPUFAs), specifically very long chain omega-3 fatty acids (VLCn3s), as well as compositions comprising high concentrations of such VLCn3s, from natural oils. Breivik and Svensen further disclose that there is only a small amounts of the VLCn3s in natural oils like fish oils, and explains why these and other very long chain fatty acids are substantially removed during production of traditional marine omega-3 concentrates, where the aim is to up-concentrate omega-3-fatty acids with chain length C20-C22.

In the start of the Discussion section of a recently published meta-analysis on the efficacy of omega-3 fatty acid supplementation for treatment of DED, Giannaccare et al. (2019) Efficacy of omega-3 fatty acid supplementation for treatment of Dry Eye Disease: A meta-analysis of randomized clinical trials, Cornea 38 (5) 565-573, the authors state that the effect of both dietary consumption and supplementation of omega-3 fatty acids on signs and symptoms of DED is still dubious. However, based on their study, including 17 randomized clinical studies involving 3363 patients, the authors conclude that omega-3 fatty acid supplementation improves dry eye symptoms, tear film stability and tear production in patients with DED. On the other hand, the authors comment observed substantial heterogenicity for all their outcome variables, entailing that the results were not consistent across the studies. In the Discussion section we find a number of statements as to this heterogenicity, including the following: "Although we performed meta-regression and sub-group analysis, unexplained heterogeneity remained. This inconsistency limits our confidence in the reported estimates and their generalizability", " . . . we could not identify any relationship between the efficacy and the dose and duration of treatment", " . . . the difference in corneal fluorescein staining between the groups was not stable after sensitivity analysis", "Therefore, this result should be interpreted by caution". It becomes clear that Giannaccare et al. in their study, which was published after the priority date of the present application, did not realise what was disclosed by the inventors of the present invention:

It has now surprisingly been found that the focus on C20-C22 omega-3 acids (EPA+DHA) for alleviating symptoms and for treatment of DED, at the best only presents a limited benefit for patients suffering from DED, and that a more efficient benefit for alleviating symptoms and treatment of this common and costly disease can be obtained by administration of compositions comprising VLCFAs, including VLCn3s. Further, compositions containing VLCFAs suitable for oral and local applications are disclosed, for use in treatment of DED.

When the applicant looked into published studies that are included in the meta-analysis by Giannaccare et al., it appears that studies based on vegetable oils and on marine omega-3 concentrates, where VLCFAs are absent or assumed to be substantially removed in order to concentrate the desired C20-C22 omega-3 acids, tend to show no or limited positive effects on DED, while studies that are based on non-concentrated fish oils and krill oil tend to give clearly positive results for DED patients. This surprising connection between omega-3 fatty acid source and effect, has eluded the authors of the meta-analysis, and also the authors of the individual studies that were included in the meta-study.

As used herein the term "treating" or "treatment" refers to 1) inhibiting the disease; for example, inhibiting a disease, condition or disorder in an individual who is experiencing or displaying the pathology or symptomatology of the disease, condition or disorder, including prevention of the disease, condition or disorder (i.e. prophylactic treatment, arresting further development of the pathology and/or symptomatology), or 2) alleviating the symptoms of the disease; for example by alleviating the symptoms of DED, or 3) ameliorating the disease; for example, ameliorating a disease, condition or disorder in an individual who is experiencing or displaying the pathology or symptomatology of the disease, condition or disorder (i.e., reversing the pathology and/or symptomatology). Particularly, in one embodiment the composition for use is for preventive treatment, such as for maintaining normal meibum function, or improving meibum function, by supplying the meibum with the compositions comprising VLCFAs.

The terms "administer," "administration," and "administering" as used herein refer to (1) providing, giving, dosing and/or prescribing by either a health practitioner a composition according to the present disclosure, and (2) putting into, taking, applying or consuming by the human patient or person himself or herself, or non-human mammal a composition according to the present disclosure.

The lipid composition of meibum is different from the lipid composition of virtually any other tissues in the human body. Butovitch (Experimental Eye Research (2017) 163: 2-16) describes a number of lipid components in human meibum together with their percentage of total lipids: (O)-Acetylated ω-hydroxy fatty acids (OAHFA) (1-5%), cholesteryl esters (30-40%), ceramides (traces), cholesteryl esters of OAHFA (3%), diacetylated diols (not quantitated), free fatty acids (up to 1%), phospholipids and sphingomyelins (up to 0.1%), glycerides (1%, mostly as triolein), wax esters (30-48%). The main polar lipids secreted from meibomian glands are OAHFAs, and these fatty acids act as the main surfactants among the meibomian lipids (Millar et al. Meibomian Glands and Lipid Layer, update of Encyclopaedia of the Eye, 2010, Pages 13-20; Elsevier Inc. 2017). In human meibomian wax esters most fatty acids are based on C14-C20 fatty acids, but also VLC fatty acids reaching a chain length of at least C32 are present.

The invention provides a composition comprising very long chain polyunsaturated fatty acids derived from natural oils, for treatment of dry eye disease (DED) and meibomianitis. In a first embodiment, the composition comprises at least 1%, such as at least 2% or 3%, or more preferably at least 5% by weight of VLCPUFA, such as at least 10%, such as at least 20%, such as at least 25% by weight of VLCPUFAs. Typically, such compositions may comprise more than 10%, more than 20%, more than 30%, more than 40%, more than 50%, more than 60%, or more than 70% by weight of very long chain polyunsaturated fatty acids, such as up to about 80% VLCPUFAs. The compositions for use may also comprise other VLCFAs than VLCPUFAs/VLCn3s; such as very long chain monounsaturated fatty acids (VLCMUFAs). In some embodiments, the inclusion of such VLCMUFAs is preferred. In one embodiment, the composition for use comprises at least 0.5%, such as at least 1%, such as at least 2% by weight of VLCMUFAs. More preferably, the composition comprises at least 4% by weight of VLCMUFAs, such as more than 5%, more than 8%, more than 15%, more than 20%, more than 30%, more than 40%, more than 50% or even more than 60% by weight of very long chain monounsaturated fatty acids. Preferably, the compositions comprise a mixture of different VLCUSFAs, hence comprising both monounsaturated and polyunsaturated very long chain fatty acids. In one embodiment, the VLCUSFAs content, i.e. the combined amount of VLCMUFAs and VLCPUFAs, is at least 5% by weight of the composition. VLCMUFAs that may be present in the compositions are selected from any one of, including but not limited to, the following group of fatty acids: C24:1 (tetraconsenoic acid (nervonic acid)), C26:1 (hexacosenoic acid), C28:1 (octacosenoic acid), C30:1 and C32:1. Further, in some embodiments, the composition comprises very long chain saturated fatty acids (VLCSFAs). E.g. the composition comprises more than 1.0%, such as more than 2.0% of VLCSFAs.

Without limiting us to the discussion above, or other specific biological mechanisms, we here disclose compositions containing VLCPUFAs and other VLCFAs obtained from natural sources that can be utilised to treat DED, such as to alleviate the effects of DED. Compositions according to the present invention can, inter alia, be manufactured based on natural oils and methods according to those that are disclosed in patent application WO2016/182452, but are not limited to the starting oils and methods that are disclosed in that application.

In one embodiment, the VLCPUFAs originate from a natural oil selected from the group of fish oil, squid oil, krill oil, copepod oil and algal oil. As will be disclosed in more detail below, further natural sources for compositions according to the present invention are the copepod *Calanus finmarchicus* and other *Calanus* species, as well as the krill *Euphausia crystallorphias*, and other marine species containing a high relative amount of wax esters among their lipid classes. In one embodiment, the VLCFAs, including the VLCPUFAs, of the composition is unmodified as compared to the oil isolated from the natural source. Hence, in one embodiment, the chain length of the VLCPUFAs are unmodified, and preferably, the natural VLCPUFAs are included in the compositions, without any steps for elongations having taken place prior to administration. Further, the compositions do not comprise any lipid producing cells that secrete or produce the VLCPUFAs. Rather, the compositions comprise a certain amount of VLCFAs, including VLCPUFAs and optionally VLCMUFAs, wherein the VLCFAs are isolated and up-concentrated from a natural source, using a method suitable for up-scaling and production for commercial use. One suitable method for preparation is disclosed in WO2016/182452. Fatty acids are generally instable, and the fatty acids for use are to be prepared by methods wherein mild conditions are used (e.g. low temperature and pressure) to avoid degradation and isomerisation, e.g. to avoid that the natural all-cis-fatty acids are amended to trans-fatty acids or conjugated fatty acids. Some natural oils, like copepods, including oil from *Calanus finmarchicus* and other *Calanus* species, as well as the krill *Euphausia crystallorphias* have a large natural content of wax esters. This could make oil from these species well suited for the manufacture of wax ester compositions in accordance with the present invention. Isolation of enriched wax ester compositions from these oils followed by optional fractionation based on molecular size and/or degree of unsaturation would lead to wax ester compositions in accordance with the present invention, without having first to isolate suitable concentrates of fatty acid derivatives, and then having to esterify these fatty acids with fatty alcohols in order to obtain wax ester. Until now, it has not been disclosed that natural oils as mentioned above have been utilised for the treatment of DED, and it may also be of interest to note that published chemical compositions of wax esters from copepods and krill species like *Calanus finmarchicus* and *Euphausia crystallorphias* have not disclosed information on the VLCFA content of these oils.

The applicant has found that VLCFAs administered to a subject are taken up by the meibum, to provide a positive health effect. More particularly, the administered VLCFAs are transported to the meibum, or to other related specific tissue of the eye, and are taken up in such tissue which normally have VLCFAs present. Hence, the invention provides a composition comprising VLCFAs for use in treatment of DED or meibomianitis, and the use provides an increased concentration of VLCFAs in the specific tissue, which in turn ameliorates the disease or alleviates the symptoms of this. The specific tissue wherein uptake takes place is e.g. in tissue of the eyeball, including the retinas, or the meibum, and is preferably the meibum, including the meibomian glands in the eyelids. In tissues of the eye apple, uptake in tissues that are close to the eye surface, i.e. in tissues near contact with tears, including eyelids and tear ducts, is most relevant. Particularly, the treatment may be for maintaining normal tissue function by supplying the tissues with VLCFAs, wherein the administered VLCFAs can help maintain good functions in tissues known to normally have the VLCFAs present. For example, the addition of the VLCFAs to the different tissues can contribute to a direct, amended or improved fluidity of cell membranes. The Example 1 below includes a feeding study in mice, and this showed that orally administered very long chain fatty acids are taken up by the meibomian glands. The eye tissue from mice fed a diet comprising VLCPUFAs had higher levels of VLCPUFAs in the meibomian glands than the controls, fed a diet without VLCPUFAs present. Based on these results, combined with the knowledge that omega-3 fatty acid supplementation improves dry eye symptoms, tear film stability and tear production in patients with DED, the applicant has inferred that very long chain fatty acids are useful in the treatment of dry eyes disease and meibomianitis. The Example 2 below includes a feeding study in mice, and this shows that orally administered very long chain fatty acids are taken up by tissue of the whole eye. Hence, the applicant has shown that VLCFAs supplemented through feed are taken up by eye tissue, and are not only synthesised there. The administered VLCFAs, taken up particularly by the tissue close to the eye apple surface, can hence contribute to the treatment of DED and meibomianitis.

In addition to the VLCPUFAs, the composition may further comprise other fatty acids, such as further long chain polyunsaturated fatty acids, and/or further VLCFAs such as VLCMUFAs. In one embodiment, the composition for use comprises at least 5% by weight of one or more LCPUFA, such as one or more C20-C22 PUFAs. In certain embodiments, such compositions of this invention comprise at least 25 percent, at least 30 percent, at least 40 percent, at least 50 percent, at least 60 percent, or at least 70 percent by weight of at least one LCPUFA, such as one or more C20-C22 long chain PUFAs. In one embodiment, the LCPUFAs comprise at least one of EPA, DHA and omega-3 DPA (all-cis-7,10, 13, 16,19-docosapentaenoic acid). Further, in other embodiments, the compositions of this invention comprise at least 5 percent, at least 8 percent, or at least 10 percent by weight of DPA (22:5n3). In some embodiments of the present invention, the weight ratio of EPA:DHA of the composition ranges from about 1:15 to about 10:1, from about 1:10 to about 8:1, from about 1:8 to about 6:1, from about 1:5 to about 5:1, from about 1:4 to about 4:1, from about 1:3 to about 3:1, or from about 1:2 to about 2:1. Preferably, there is more DHA than EPA present in the composition, and in at least one embodiment, the weight ratio of EPA:DHA of the composition ranges from about 1:3 to about 1:12. In one embodiment, the composition for use comprises 5-30% VLCPUFAs and 50-90% LCPUFAs, by weight of the composition.

The VLCPUFAs, and any other VLCFAs, of the composition have a chain length of more than 22 carbon atoms; In one embodiment, the composition comprises at least one VLCPUFA with a chain length of 24 carbons or longer. Preferably, the composition comprises a mixture of different such VLCFAs. In this regards, the VLCFAs may have chain lengths of 24, 26, 28, 30, 32, 34, 36, 38, 40 or 42 carbons. Preferably, the composition of VLCFAs comprises a mixture of at least two VLC fatty acids, and particularly with chain lengths of 24, 26, 28 and 30 carbon atoms. In particular embodiments, the composition comprises VLCPUFAs selected from any one of the, including but not limited to, 24:5n3, 24:6n3, 28:8n3 fatty acids. In one embodiment, the composition comprises at least 4%, such as at least 5%, such as about 4-10% of the 28:8n3 fatty acid. In one embodiment, the composition for use comprises 5-15% EPA, 5-15% DPA, 35-55% DHA and at least 5% VLCPUFAs, by weight, and more preferably the VLCPUFAs of the composition comprise the 28:8n3 fatty acid. Preferably, the composition further comprises VLCMUFAs, such as at least 0.5 weight % VLCMUFAs.

The fatty acids of the compositions, both the VLCPUFAs and other fatty acids of the compositions, can be in the form of free fatty acids, fatty acid salts, mono-, di-, triglycerides, ethyl esters, wax esters, OAHFAs, cholesteryl esters, ceramides, phospholipids or sphingomyelins, alone or in combination. Or, the fatty acids may be in any form that can be absorbed in the digestive tract, or that can be absorbed by the meibomian glands by local application, or wherein the fatty acids function as lubricates at least partly replacing the lipids of the meibum. Preferably, the fatty acids are in the form of free fatty acids, fatty acid salts, ethyl esters, glycerides or wax esters. For local applications, delivering preparations comprising the VLCPUFAs/VLCFAs compositions, the fatty acids are preferably in the form of free fatty acids, fatty acid salts, as glycerides (mono- di- or triglycerides alone or in combinations), OAHFAs, cholesteryl esters, ceramides, phospholipids, sphingomyelins or wax esters, and in an even more preferred embodiment the VLCPUFAs/VLCFAs are in the form of wax esters. In one embodiment, for the local application of the composition, this comprises salts, and accordingly at least some of the fatty acids of the composition, such as at least some of the VLCPUFAs, may be in the form of fatty acid salts. The administered VLCFAs may also change form in vivo as endogenic biological systems may transfer VLCFAs into another form, such as to w-hydroxy fatty acids, including (O-acyl) w-hydroxy FAs (OAHFAs), or to cholesteryl esters, ceramides, free fatty acids, phospholipids, sphingomyelins and wax esters.

The composition presently disclosed may comprise at least one non-active pharmaceutical ingredient, i.e., excipient. The choice of such excipients depends on several factors, including the administration form. Non-active ingredients may solubilize, suspend, thicken, dilute, emulsify, stabilize, preserve, protect, colour, flavour, and/or fashion active ingredients into an applicable and efficacious preparation, such that it may be safe, convenient, and/or otherwise acceptable for use. Examples of excipients include, but are not limited to, solvents, carriers, diluents, binders, fillers, sweeteners, aromas, pH modifiers, viscosity modifiers, antioxidants, extenders, humectants, disintegrating agents, solution-retarding agents, absorption accelerators, wetting agents, absorbents, lubricants, colouring agents, dispersing agents, emulsifiers, surfactants and preservatives. Excipients may have more than one role or function, or may be classified in more than one group; classifications are descriptive only and are not intended to be limiting. In some embodiments, for example, the at least one excipient may be chosen from corn starch, lactose, glucose, microcrystalline cellulose, magnesium stearate, polyvinylpyrrolidone, citric acid, tartaric acid, water, ethanol, glycerol, sorbitol, polyethylene glycol, propylene glycol, cetylstearyl alcohol, carboxymethylcellulose, and fatty substances such as hard fat or suitable mixtures thereof. Aqueous solutions suitable for local treatment of the eye can include any of preservatives, surfactants, buffers, salts, tonicity agents, emulsifiers and water. In some embodiments, the compositions presently disclosed comprise a pharmaceutically acceptable antioxidant, e.g., tocopherol such as alpha-tocopherol, beta-tocopherol, gamma-tocopherol, and delta-tocopherol, or mixtures thereof, BHA such as 2-tert-butyl-4-hydroxyanisole and 3-tert-butyl-4-hydroxyanisole, or mixtures thereof and BHT (3,5-di-tert-butyl-4-hydroxytoluene), or ascorbyl palmitate or mixtures thereof. Optionally, for local applications in or to the eye the use of antioxidants and preservatives could preferably be avoided. For instance, the composition for use may be included in a preparation packed as a single dose unit, or in multi-dose bottles, suitable for dispensing preservative-free eye drops. Hence, the compositions of VLCFAs can be combined with other active ingredients from for instance plant extracts. Natural antioxidants like beta-carotene, a source of Vitamin A, which may contribute to the maintenance of normal vision can be a useful ingredient. Likewise, Vitamin E (preferably as the natural RRR-tocopherols or d-tocopherols) which can contribute to the protection of cells from oxidative damage may be useful to include. Lutein and zeaxanthin are carotenoids which can be included, which the human body may enrich at the macula of the retina and the lens.

In further aspects, the invention provides a method for treatment of DED and meibomianitis of a subject, comprising administering to the subject a composition comprising VLCPUFAs derived from natural oils. The method comprises administering to the subject a therapeutically effective amount of the composition comprising at least 1% VLCPUFAs, such as at least 5% VLCPUFAs.

The embodiments and features described in the context of the first aspect directed to the composition for use, also apply to this other aspect of the invention directed to the method for treatment.

It is known that individuals may experience reduced ability for endogenic synthesis of VLCFAs, including VLC-MUFA and VLCPUFA acids in specific tissues where these fatty acids are needed for maintaining the individuals' optimal health. However, to the best of our knowledge, not until the present application has it been disclosed that deficiencies in one or more elongase system may affect the meibum in manners that could explain why concentrates of C20-C22 omega-3 fatty acids, where the VLCFAs have been substantially removed, do not display significant positive effects to alleviate DED. In one embodiment, the method or composition for use is for treatment of a patient having deficiencies in one or more elongase systems of the eye, e.g. to compensate for the deficient endogenic synthesis of VLCPUFAs.

Endogenic biological systems other than the elongase systems may be utilised to transfer LCFAs, including VLC-MUFAs and VLCFAs, into the beneficial (O-acyl)-w-hydroxy FAs (OAHFAs), cholesteryl esters, ceramides, free fatty acids, phospholipids, sphingomyelins and wax esters. The composition according to the invention comprising VLCFAs, although wherein the fatty acids are on another form than w-hydroxy fatty acids, can be used to provide these very important fatty acids to the relevant tissue, e.g. to the meibum. Hence, the term VLCFAs as used here is to be understood to include further in vivo transformations of the VLCFAs. As an example, the term includes hydroxy-derivatives of VLCFAs as formed in vivo, including w-hydroxy VLCFAs, and further in vivo transformations of the w-hydroxy VLCFAs.

The compositions for use disclosed herein are intended to be taken orally or to be applied locally in or around the eyes and eyelids. In one embodiment, the composition disclosed is included as an ingredient in preparations for local application. In in one aspect, the invention provides an ophthalmic formulation comprising a composition as disclosed and claimed. Hence, the invention provides an ophthalmic formulation comprising a composition comprising at least 1%, e.g. at least 5%, by weight of very long chain polyunsaturated fatty acids derived from natural oils. The embodiments and features described in the context of the first aspect directed to the composition for use, also apply to this other aspect of the invention directed to the formulation for use in treatment. For local application, such ophthalmic formulation, i.e. preparation, may be in the form of, for example, eye drops, sprays, ointments, creams, salves, lotions, gels, ocular mini tablets and the like. Such topical administration to an eye or ophthalmic tissue includes any surface of the eye anatomy that is, or can be, topically exposed. Preferably, the compositions are administered to the cornea or conjunctiva, to the upper or lower eyelid margins, meibomian gland ducts, eyelashes or any area of the eye or eye lid anatomy. Such local application may induce one or more actions, such as creating a seal when the eyes are closed, by interacting with the tear film, enhancing the tears by spreading them evenly and maintaining a consistent quality of vision, by covering the tear film thereby slowing the rate of tear evaporation, and by alleviation inflammatory actions in or around the eyes and meibomian glands. Such ophthalmic formulations, e.g. as formulations of spray, drops or creams for direct application to the eye, eyelids or skin around the eye, can consist of various ingredients and concentration of the VLCFAs. Typical concentrations of VLCFAs in an ophthalmic formulation, such as in a spray or eye drops, may be from 0.1% to 1%, or up to 2%, VLCPUFAs and optionally 0.01 to 1% VLCMUFAs, by weight % of the total topic formulation. Other ingredients can be the active ingredient Sodium Hyaluronate. Hyaluronate supports the water binding capacity of the tear fluid and protects the cells against damage. Purified water, polyoxyethylene sorbitan monooleate, glycerol, sorbitan monooleate, citric acid monohydrate, trometamol, potassium chloride and sodium chloride are relevant ingredients for making an emulsion for application as a fluid and for smoothening the skin.

Formulation of creams for direct application to the eyelids or skin around the eye can consist of various ingredients and concentrations of the VLCFAs. A typical concentration of VLCFAs in a cream can be from 1% to 2%, or up to 5% or even up to 10% VLCPUFAs and optionally 0.01 to 5% VLCMUFAs, by weight % of the total topic formulation. Other ingredients can be the active ingredient sodium hyaluronate. Other ingredients typical for making the cream emulsion and for smoothen and strengthen the skin will also be relevant. Examples of such ingredients are water, cetearyl alcohol, dicaprylyl ether, sodium lactate, polysorbate, cetyl palmitate, sorbitan stearate, dehydroacetate, sodium benzoate and oils and extracts from plant materials.

In some embodiments of the invention for local applications, OAHFAs and cholesterol esters of OAHFAs, are preferred surfactants, either alone or together with other surfactants and/or emulsifiers. In one embodiment, VLCPUFAs on the form of OAHFAs, are included in the composition for use. The optional other surfactants and/or emulsifiers are selected to provide a stable formulation, which e.g. may not need to be shaken before use. In some embodiments, the compositions presently disclosed comprise a pharmaceutically acceptable surfactant and/or emulsifier selected from the group of polysorbates; e.g. Polysorbate 80, and polyacrylic acids (e.g. Carbomer).

The compositions are for treatment of eye disorders, and particularly to alleviate or relieve ocular symptoms associated with ophthalmic disorders or conditions, including dry eye disease (keratoconjunctivitis sicca) and meibomian gland dysfunction. In a further embodiment, the compositions of the invention can be used for the palliative treatment and care of the eye or ophthalmic tissue. Also, as mentioned in the background of the invention, some medications have a negative effect on meibomian glands. The compositions disclosed can have a beneficial effect when used by patients being on medications having dry eye symptoms as side effects. Further, the composition may be offered as a supplement for maintaining healthy eyes and preventing dry eye diseases and discomfort to develop—as a person is aging or is exposed to dry eye diseases because of environmental conditions, medication or health related factors. And even further, the composition may be used for treatment and alleviation of dry eye discomfort linked to aging, menopausal and other hormonal changes, various diseases like autoimmune disorders like lupus, rheumatoid arthritis, scleroderma or Sjögren's Syndrome, allergies, diabetes, side-effects of various medication, dry environment, use of contact lenses, high computer and television time. It is further presumed, that the compositions disclosed are useful in the treatment of other ophthalmological disorders, such as those associated with neovascularization in a subject, such as wherein the neovascularization is corneal, retinal, choroidal, uveal, or iris neovascularization. In some embodiments, the ophthalmological disorder associated with neovascularization is age-related macular degeneration (AMD), Stargardt's disease, retinopathy, retinopathy of prematurity (ROP), diabetic retinopathy, retinal vein occlusion, sickle cell retinopathy, radiation retinopathy, iritis, or conjunctivitis.

Treatment as disclosed could preferentially be combined with recommended procedures for external treatment of the meibomian glands, like lid scrubs, warm compresses and gentle lid compression and massage.

For oral use, the compositions presently disclosed may be formulated in variable forms, such as in oral administration forms, e.g., tablets or soft or hard capsules, chewable capsules or beads, or alternatively as a fluid composition. By intake of concentrates of the VLCFA fraction of the natural oils, i.e. the composition of the invention, the patients benefit from higher positive effects, as well as much lower volume of medicine/supplement than by consuming natural oils like fish oil, krill oil, algal oil or calanus oil, in non-concentrated form. At the same time the patient will benefit from the absence of caloric intake and potential negative effects of fatty acids and lipid components that do not promote alleviation and/or healing of DED and meibomianitis. In one embodiment, the compositions disclosed are included in preparations for oral intake. For oral administration, the compositions may be administered, e.g., in the form of capsules, tablets or any other drug delivery forms. For example, the composition may be encapsulated, such as in a gelatine capsule. In some embodiments of the present disclosure, the capsule fill content ranges from about 0.400 g to about 1.600 g. For example, in some embodiments, the capsule fill content ranges from about 0.400 g to about 1.300 g, from about 0.600 g to about 1.200 g, from about 0.600 g to about 0.800 g, from about 0.800 g to about 1.000, from about 1.000 g to about 1.200 g, or any amount in between. For example, in some embodiments the capsule fill content is about 0.600 g, about 0.800 g, about 1.000 g, or about 1.200 g.

For local applications, non-concentrated natural oils represent impractical and/or prohibitive large volumes that would blur the vision as well as resulting in staining the skin, while the disclosed concentrates of active fatty acid components can be utilised without similar problems. The dose and concentration of the VLCPUFA-composition to be administered locally to the eye should be adjusted with the additional components of the preparation, and is dependent on the form of the preparation. The skilled person will be able to test and adjust to identify an optimal dose and concentration. A preparation for local administration to the eye may be applied at least ones daily, such as in the morning and in the evening.

It is understood that the skilled artisan will envision additional embodiments consistent with the disclosure provided herein.

EXAMPLES

Example 1: Supplementation with VLCPUFA in Mice—Effect on Fatty Acid Composition of Meibomian Glands Two types of marine lipid concentrates (Lipidmix 1 and Lipidmix 2) were tested in a feeding study in mice. Lipidmix 1 and 2 were prepared from a standard anchovy fish oil. The crude fish oil was purified and ethylated, the ethylated oil was fractionated and up-concentrated by short path distillation and urea precipitation, and for Lipidmix 1 Lithium-precipitation was performed, to obtain the desired composition. The fractions were finally re-esterified to triglycerides by an enzymatic reaction with glycerol.

Epax Norway prepared the two different lipidmixes which were included in mice feed pellets. The fatty acids of the lipidmixes were on triglyceride (TG) form, containing small amounts of mono- and diglycerides.

The fatty acid compositions of Lipidmix 1 and 2 were analysed on a Scion 436-GC with a split/splitless injector (splitless 1 min), using a Restek Rxi-5 ms capillary column (length 30 m, internal diameter 0.25 mm, and film thickness 0.25 μM), flame ionization detector and TotalChrom Software. The carrier gas was hydrogen. The amount of fatty acids was calculated using C23:0, EPA and DHA standards. Same response factor as DHA was assumed for the VLCPUFAs, as no standards are available.

The fatty acid compositions of Lipidmix 1 and 2 are shown in Table 1.

TABLE 1

Composition of Lipidmix 1 and 2

|  | Lipidmix 1 (mg/g) | Lipidmix 2 (mg/g) |
| --- | --- | --- |
| EPA | 24 | 28 |
| DPA | 45 | 39 |
| DHA | 151 | 191 |
| C24:4 | 5 | 0 |
| C24:5 | 68 | 1 |
| C24:6 | 33 | 1 |
| C26:3 | 2 | 0 |
| C26:4 | 7 | 0 |
| C26:5 | 20 | 0 |
| C26:6 | 62 | 0 |
| C26:7 | 9 | 0 |
| C28:4 | 2 | 0 |
| C28:5 | 10 | 0 |
| C28:6 | 14 | 0 |
| C28:7 | 4 | 0 |
| C28:8 | 163 | 0 |
| C24:1 | 20 | 0 |
| C26:1 | 3 | 0 |
| Total VLCPUFA (C24-C28) | 323 | 2 |
| Total VLCMUFA (C24-C26) | 23 | 0 |

Test Diets:

Test Diet 1: 10% fat (5% soybean oil, 5% lard), 17% protein, 5% fibre, 62% carbohydrates, minerals, vitamins.

Test Diet 2: 10% fat (5% Lipidmix1, 5% lard), 17% protein, 5% fibre, 62% carbohydrates, minerals, vitamins.

Test Diet 3: 10% fat (5% Lipidmix2, 5% lard), 17% protein, 5% fibre, 62% carbohydrates, minerals, vitamins.

Hence, the Test Diet 1 is a standard mice diet. Test Diet 2 comprises fish oil concentrate including VLCPUFAs and VLCMUFAs. Test Diet 3 comprises fish oil concentrate without VLCPUFAs or VLCMUFAs.

All test diets were stored at −20° C. until thawing and feeding ad libitum.

Animals:

Mice from the strain C57/bl6 from Charles River were used in the feeding study. The body weight was around 25 g. The animals were housed in cages with free access to food and water at room temperature.

Meibomian Glands:

5 mice from each test diet groups were sacrificed 33 days after start of the feeding study. Meibomian glands were carefully dissected from the mice eyelids by trained personnel. The samples were immediately frozen on dry ice and shipped to Epax Norway for fatty acid analyses.

Sample Preparation:

1 ml of a solution containing 0.05157 mg/ml C23:0 internal standard was added to a test tube and the solvent was evaporated under a stream of nitrogen. The same test tube was then added the meibomian glands and the weight of tissue was noted. 3.5 ml of a solution containing 0.5 M Sodium methoxide in methanol was added and the test tube was then heated in a boiling water bath for 1 hour. After cooling 5 ml of $BCl_3$ was added and the test tube was heated in the boiling bath for 5 min. After heating the test tube was added 0.6 ml of isooctane and washed with 5 ml of saturated sodium chloride in water. The isooctane phase was transferred to micro-vials and injected directly on the GC.

Fatty Acid Analyses of Meibomian Gland Tissue:

The fatty acid analysis of extracts comprising meibomian gland tissue was done on a Perkin Elmer, Clarius 680/600T GC-MS using an Agilent CP Wax 52 B (CP7713) column. The peak areal from the chromatogram of three single ions scans (SIM of 67, 79 and 91 m/z) were used for quantification of the LC and VLCPUFAs. The response factor for DHA (relative to C23:0) was calculated by using standard solutions with known concentrations of DHA and C23:0. As no standards are available for the VLCPUFAs, the same response factor as for DHA was assumed, and used to calculate mg fatty acid/g tissue for the VLCPUFA. The content of the VLCMUFA C24:1 in the tissue was calculated from the full scan chromatogram, assuming the same response factor as for C23:0.

The results of the analysis of PUFAs with 22 carbons or more are shown in Table 2 below. The results for each fatty acid are further shown in FIGS. 1 to 9, wherein FIG. 1 provides the content of DHA (mg/g tissue) in meibomian glands from mice fed Test Diets 1, 2 or 3.

Figure 2:
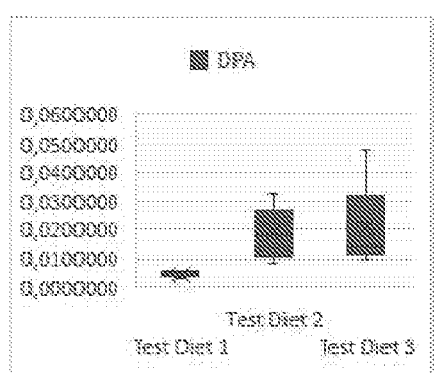

FIG. 2 provides the content of DPA (mg/g tissue) in meibomian glands from mice fed Test Diets 1, 2 or 3.

Figure 3:
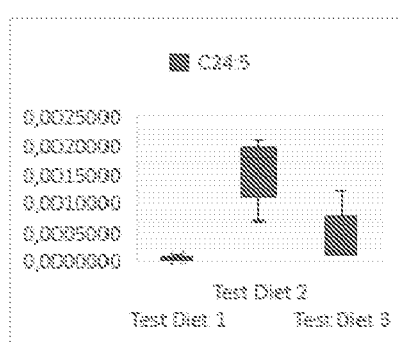

FIG. 3 provides the content of C24:5 (mg/g tissue) in meibomian glands from mice fed Test Diets 1, 2 or 3.

Figure 4:
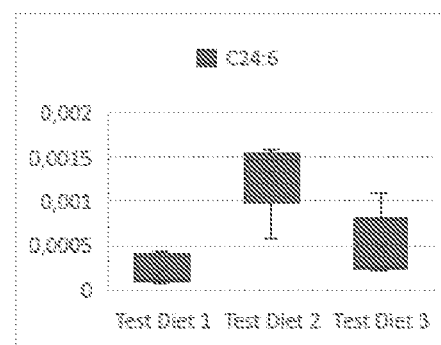

FIG. 4 provides the content of c24:6 (mg/g tissue) in meibomian glands from mice fed Test Diets 1, 2 or 3.

Figure 5:
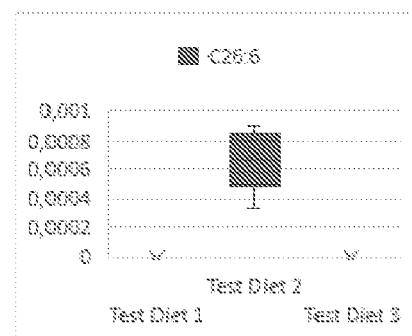

FIG. 5 provides the content of c26:6 (mg/g tissue) in meibomian glands from mice fed Test Diets 1, 2 or 3.

Figure 6:
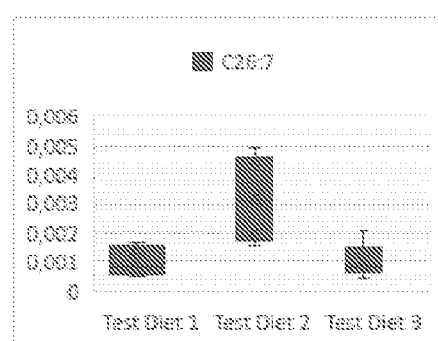

FIG. 6 provides the content of c26:7 (mg/g tissue) in meibomian glands from mice fed Test Diets 1, 2 or 3.

Figure 7:
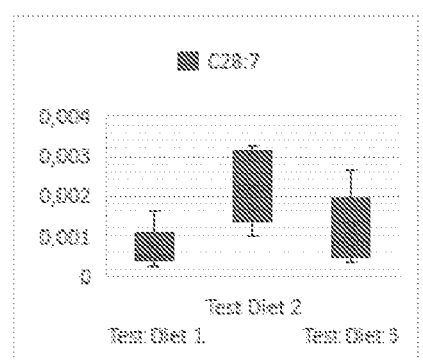

FIG. 7 provides the content of C28:7 (mg/g tissue) in meibomian glands from mice fed Test Diets 1, 2 or 3.

Figure 8:
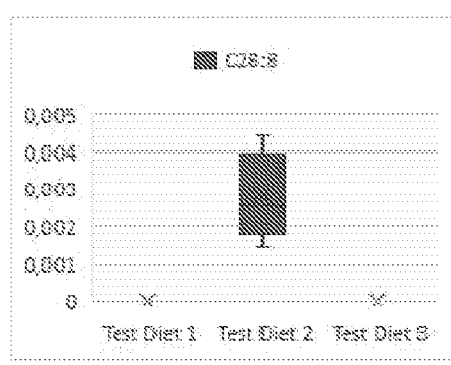

FIG. 8 provides the content of C28:8 (mg/g tissue) in meibomian glands from mice fed Test Diets 1, 2 or 3.

Figure 9:
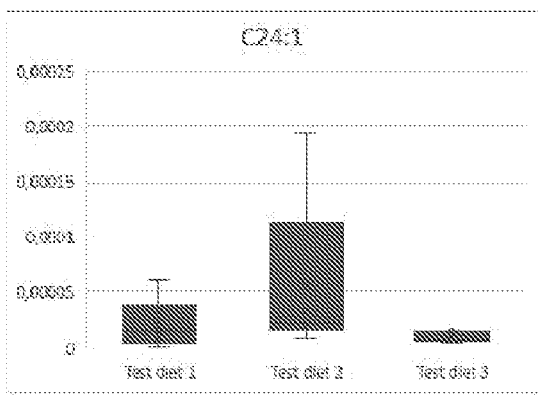

FIG. 9 provides the content of C24:1 (mg/g tissue) in meibomian glands from mice fed Test Diet 1, 2 and 3.

TABLE 2

Calculated amount of fatty acids in meibomian gland tissue of mice.

| Id. | DHA mg/g tissue | DPA mg/g tissue | C24:5 mg/g tissue | C24:6 mg/g tissue | C26:6 mg/g tissue | C26:7 mg/g tissue | C28:7 mg/g tissue | C28:8 mg/g tissue | C24:1 mg/g tissue |
|---|---|---|---|---|---|---|---|---|---|
| Results for Test Diet No 1: | | | | | | | | | |
| 15 | 0.04055 | 0.00465 | 0.00005 | 0.000063 | 0 | 0.000638 | 0.000538 | 0 | 0.00161 |
| 11 | 0.04941 | 0.00367 | 0.00000 | 0.000415 | 0 | 0.000534 | 0.000465 | 0 | 0.00694 |
| 12 | 0.04893 | 0.00543 | 0.00009 | 0.000387 | 0 | 0.001708 | 0.000261 | 0 | 0.06114 |
| 13 | 0.04650 | 0.00512 | 0.00003 | 0.000112 | 0 | 0.000806 | 0.000605 | 0 | 0.01656 |
| 17 | 0.04031 | 0.00602 | 0.00001 | 0.000111 | 0 | 0.001363 | 0.001595 | 0 | 0.01506 |
| Results for Test Diet No. 2: | | | | | | | | | |
| 22 | 0.11136 | 0.01390 | 0.00178 | 0.001578 | 0.00081 | 0.001953 | 0.001724 | 0.003423 | 0.02071 |
| 23 | 0.13559 | 0.01802 | 0.00157 | 0.001384 | 0.00082 | 0.003124 | 0.002985 | 0.002598 | 0.02190 |
| 24 | 0.08243 | 0.00856 | 0.00070 | 0.000572 | 0.00034 | 0.001581 | 0.000996 | 0.002138 | 0.00922 |
| 25 | 0.14084 | 0.02033 | 0.00210 | 0.001516 | 0.00063 | 0.004329 | 0.002145 | 0.001488 | 0.19397 |
| 29 | 0.20111 | 0.03322 | 0.00180 | 0.001455 | 0.00088 | 0.004914 | 0.003260 | 0.004492 | 0.03202 |
| Results for Test Diet No. 3: | | | | | | | | | |
| 32 | 0.17862 | 0.01721 | 0.00011 | 0.000547 | 0 | 0.002082 | 0.001215 | 0 | 0.00752 |
| 33 | 0.13642 | 0.01375 | 0.00013 | 0.000261 | 0 | 0.000824 | 0.000851 | 0 | 0.01417 |
| 34 | 0.09671 | 0.00981 | 0.00017 | 0.000216 | 0 | 0.000440 | 0.000332 | 0 | 0.00500 |
| 35 | 0.07746 | 0.01490 | 0.00028 | 0.000258 | 0 | 0.000839 | 0.000600 | 0 | 0.00771 |
| 36 | 0.32662 | 0.04785 | 0.00122 | 0.001084 | 0 | 0.000904 | 0.002654 | 0 | 0.01425 |

The results above show that there are significantly higher levels of DPA and DHA in the meibomian tissue of mice given Test Diet no. 2 and 3, than for mice given Test Diet 1. These diets contain similar amounts of DPA and DHA.

The meibomian glands from mice fed Test Diet 2 (comprising VLCPUFAs and VLCMUFAs) show significant higher levels of VLCPUFAs than meibomian glands from mice fed Test Diet 1 and 3. Especially for the VLCPUFAs C26:6 and C28:8 this is very clear. FIG. 8 illustrates this very clear difference, with no signal for C28:8 for Test Diet 1 and 3, with a clear peak for Test Diet 2.

The feeding study in mice showed that orally administered VLC fatty acids were taken up by the meibomian glands. This eye tissue from mice with VLCPUFA in the diet had higher levels of VLCPUFAs in the meibomian glands than the controls.

This example supports the invention that a composition of VLCFAs are taken up by the meibomian gland tissue and can be used for treatment of Dry Eye Disease and meibomianitis.

Example 2: Supplementation with VLCPUFA in Mice—Effect on Fatty Acid Composition of Eye (Eye Apple)

Lipid Compositions:

The same lipid mixes, Lipidmix 1 and 2, and the same Test Diets, Test Diets 1, 2 and 3, as used in Example 1 were used in this Example.

Animals:

Mice from the strain C57/bl6 from Charles River were used in the feeding study. The body weight was around 25 g. The animals were housed in cages with free access to food and water at room temperature.

Eye Apple Tissue 8 individuals from Test Diet group 1 and 9 individuals from Test Diet groups 2 and 3 were sacrificed 29-33 days after start of feeding study. The whole eye apples, containing retinal tissue, were carefully dissected from the animals by trained personnel. The samples were immediately frozen on dry ice and shipped to Nofima, Norway, for extraction and separation of phospholipid (PL). The fatty acid analyses of prepared samples were done at Epax Norway. Total lipids were extracted from the mice eye tissues by the method by Folch, J. Lees, M, Sloane Stanley G H. A simple method for the isolation and purification of total lipids from animal tissues. J Biol Chem. 1957; 226(1):497-509. PMID: 13428781. Lipid classes were separated using thin layer chromatography (TLC). The phospholipid fractions were used for the fatty acid analyses.

Fatty Acid Analyses of Whole Eye Samples:

The fatty acid analysis was done on a Perkin Elmer, Clarius 680/600T GC-MS using an Agilent CP Wax 52 B (CP7713) column. The peak area from chromatograms obtained from simultaneous single ions scans of 67, 79 and 91 m/z were used for quantification of the LC and VLCPUFA fatty acids. The response factor for DHA (relative to C23:0) using this setup was calculated by using standard solutions with known concentrations of DHA and C23:0. As no standards are available for the VLCPUFAs, the same response factor as for DHA was assumed, and used to calculate mg fatty acid/g tissue for the VLCPUFA.

Figure 10:
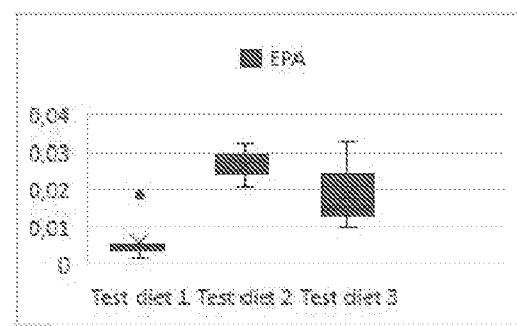
FIGS. 10 to 17 provide the content of different fatty acids in eye (apple) tissue from mice fed different test diets.

Results from Whole Eye Tissue Analysis:

The results of the analysis of PUFAs with 22 carbons or more are shown in Table 3 below, and the results for each fatty acid are shown in FIGS. 10 to 17, wherein FIG. 10. Content of EPA (mg/g tissue) in eye (apple) from mice fed Test Diet 1, 2 or 3.

Figure 11:
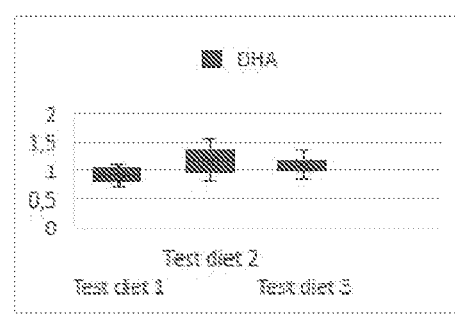

FIG. 11. Content of DHA (mg/g tissue) in eye (apple) from mice fed Test Diet 1, 2 or 3.

Figure 12:
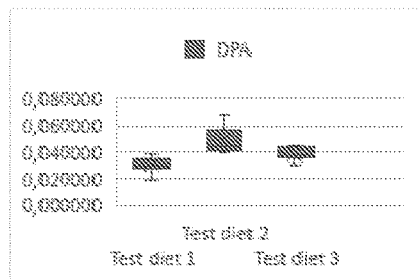

FIG. 12. Content of DPAn3 (mg/g tissue) in eye (apple) from mice fed Test Diet 1, 2 or 3.

Figure 13:
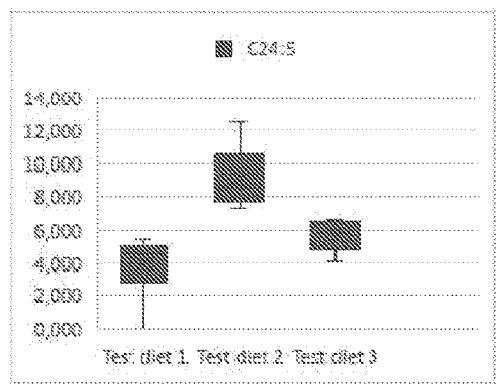

FIG. 13. Content of C24:5n3 (μg/g tissue) in eye (apple) from mice fed Test Diet 1, 2 or 3.

Figure 14:
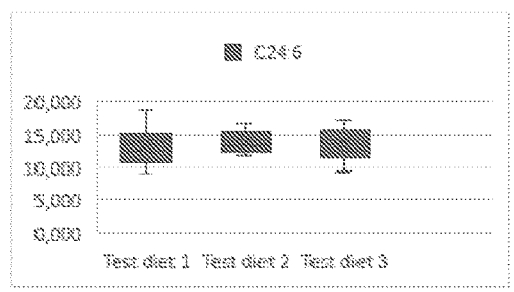

FIG. 14. Content of C24:6n3 (μg/g tissue) in eye (apple) from mice fed Test Diet 1, 2 or 3.

Figure 15:
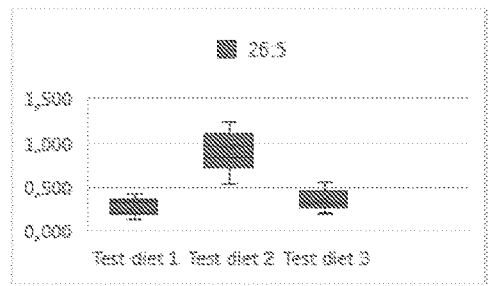

FIG. 15. Content of C26:5n3 (μg/g tissue) in eye (apple) from mice fed Test Diet 1, 2 or 3.

Figure 16:
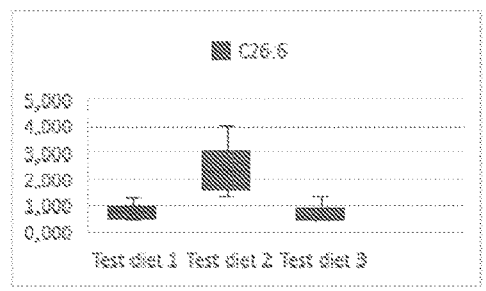

FIG. 16. Content of C26:6n3 (μg/g tissue) in eye (apple) from mice fed Test Diet 1, 2 or 3.

Figure 17:
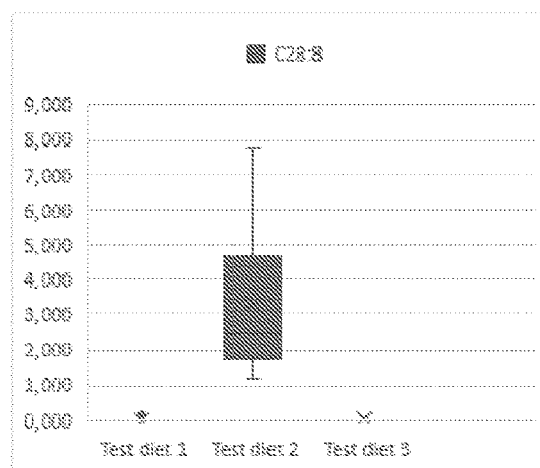

FIG. 17. Content of C28:8n3 (μg/g tissue) in eye (apple) from mice fed Test Diet 1, 2 or 3.

TABLE 3

Calculated amount of fatty acids in eye (apple) tissue of mice.

| id | Test Diet No. | EPA mg/g tissue | DHA mg/mg tissue | DPA mg/g tissue | C24:5 μg/g tissue | C24:6 μg/g tissue | 26:5 μg/g tissue | C26:6 μg/g tissue | C28:8 μg/g tissue |
|---|---|---|---|---|---|---|---|---|---|
| P 27 | 1 | 0.002 | 0.940 | 0.031 | 2.439 | 9.259 | 0.150 | 0.463 | 0.000 |
| P 28 | 1 | 0.004 | 1.024 | 0.035 | 5.120 | 15.671 | 0.207 | 0.538 | 0.000 |
| P 29 | 1 | 0.004 | 0.697 | 0.019 | 5.465 | 14.686 | 0.357 | 0.956 | 0.000 |
| P 30 | 1 | 0.006 | 0.797 | 0.028 | 4.660 | 14.076 | 0.355 | 0.993 | 0.000 |
| P 31 | 1 | 0.004 | 0.843 | 0.031 | 4.359 | 13.524 | 0.331 | 0.852 | 0.000 |
| P 32 | 1 | 0.018 | 0.813 | 0.029 | 4.112 | 10.327 | 0.322 | 0.543 | 0.142 |
| P 33 | 1 | 0.003 | 1.122 | 0.039 | 4.979 | 12.865 | 0.214 | 0.614 | 0.000 |
| P 35 | 1 | 0.005 | 1.023 | 0.035 | 0.000 | 18.822 | 0.422 | 1.258 | 0.000 |
| P 36 | 2 | 0.025 | 1.381 | 0.058 | 12.525 | 13.322 | 0.767 | 2.802 | 3.513 |
| P 37 | 2 | 0.033 | 1.240 | 0.043 | 7.302 | 13.675 | 1.164 | 1.756 | 2.151 |
| P 38 | 2 | 0.022 | 1.512 | 0.045 | 7.873 | 12.274 | 0.845 | 1.902 | 2.338 |
| P 39 | 2 | 0.021 | 1.573 | 0.069 | 8.162 | 12.776 | 0.542 | 1.372 | 1.311 |
| p 41 | 2 | 0.024 | 0.805 | 0.040 | 9.526 | 15.352 | 1.260 | 2.442 | 4.482 |
| p 42 | 2 | 0.025 | 0.827 | 0.044 | 7.646 | 11.977 | 0.786 | 3.316 | 4.801 |
| p 43 | 2 | 0.027 | 0.983 | 0.040 | 8.521 | 16.164 | 0.713 | 1.444 | 1.180 |
| p 44 | 2 | 0.030 | 1.205 | 0.051 | 10.453 | 16.906 | 0.869 | 2.312 | 2.473 |
| p 45 | 2 | 0.135 | 1.085 | 0.057 | 10.656 | 14.029 | 1.054 | 4.054 | 7.796 |
| P 16 | 3 | 0.033 | 0.891 | 0.036 | 5.979 | 17.465 | 0.305 | 0.505 | 0.000 |
| P 17 | 3 | 0.015 | 1.405 | 0.045 | 4.103 | 12.308 | 0.284 | 0.591 | 0.000 |
| P 18 | 3 | 0.019 | 0.851 | 0.031 | 6.571 | 15.349 | 0.569 | 1.363 | 0.000 |

TABLE 3-continued

Calculated amount of fatty acids in eye (apple) tissue of mice.

| id | Test Diet No. | EPA mg/g tissue | DHA mg/mg tissue | DPA mg/g tissue | C24:5 µg/g tissue | C24:6 µg/g tissue | 26:5 µg/g tissue | C26:6 µg/g tissue | C28:8 µg/g tissue |
|---|---|---|---|---|---|---|---|---|---|
| P 19 | 3 | 0.024 | 1.209 | 0.046 | 6.641 | 16.223 | 0.473 | 0.473 | 0.000 |
| P 20 | 3 | 0.026 | 1.212 | 0.043 | 5.993 | 11.142 | 0.453 | 0.734 | 0.248 |
| P 21 | 3 | 0.013 | 1.226 | 0.041 | 4.921 | 12.944 | 0.236 | 0.533 | 0.000 |
| P 22 | 3 | 0.016 | 1.091 | 0.038 | 6.097 | 15.716 | 0.294 | 0.647 | 0.000 |
| P 23 | 3 | 0.012 | 1.026 | 0.037 | 6.552 | 13.684 | 0.312 | 0.581 | 0.000 |
| P 40 | 3 | 0.010 | 1.001 | 0.037 | 4.744 | 9.479 | 0.203 | 0.511 | 0.000 |

The weight of the internal standard was 0.0974 mg.

The results of the eye apple tissue analysis show slightly higher levels of EPA, DPA and DHA in eye tissue of mice fed with the Test Diets 2 and 3 compared to control (Test Diet 1). There seems to be no difference between Test Diet 2 and 3. These diets contain similar amounts of EPA, DPA and DHA.

The PL-extracts from eye apples, containing retinal tissue, from mice fed Test Diet 2 (comprising VLCPUFAs) show higher levels of VLCPUFA than for the mice fed Test Diet 1 and 3. Especially for the VLCPUFAs C26:6 and C28:8 this is very clear.

CONCLUSION

Very long chain lipid components play an important role for the retina and retinal functions. This example supports the invention that the VLCFAs are taken up by tissue of the eye and can be used for treatment of eye diseases and in general for maintaining good eye health. The feeding studies in mice showed that orally administered VLC fatty acids were taken up by the meibum and tissues of the eye apple. Mice which had been fed with a diet comprising VLCPUFAs had higher levels of VLCPUFAs in meibum and eye tissue than controls.

The invention claimed is:

1. A method for treatment of Dry Eye Disease (DED) or meibomianitis of a subject, the method comprising administering to the subject a composition comprising at least 1% by weight of a very long chain polyunsaturated fatty acid (VLCPUFA) having a chain length of more than 22 carbon atoms, wherein the VLCPUFA is derived from a natural oil selected from the group consisting of fish oil, squid oil, krill oil, copepod oil, and algal oil.

2. The method of claim 1, wherein the composition comprises at least 5% by weight of the very long chain polyunsaturated fatty acid (VLCPUFA).

3. The method of claim 1, wherein the composition comprises at least 10% by weight of the very long chain polyunsaturated fatty acid (VLCPUFA).

4. The method of claim 1, wherein a fatty acid of the VLCPUFA is in at least one form selected from the group consisting of a free fatty acid, a fatty acid salt, a monoglyceride, a diglyceride, a triglyceride, an ethyl ester, a wax ester, an (O)-Acetylated ω-hydroxy fatty acid (OAHFA), a cholesteryl ester, a ceramide, a phospholipid, and a sphingomyelin.

5. The method of claim 1, wherein a fatty acid of the VLCPUFA is in at least one form selected from the group consisting of a free fatty acid, a fatty acid salt, an ethyl ester, a glyceride, and a wax.

6. The method of claim 1, wherein the composition further comprises at least 1% by weight of at least one very long chain monounsaturated fatty acid (VLCMUFA).

7. The method of claim 1, wherein the composition further comprises at least 5% by weight of at least one C20-C22 long chain polyunsaturated fatty acid (LCPUFA).

8. The method of claim 1, wherein the composition further comprises at least 25% by weight of at least one C20-C22 long chain polyunsaturated fatty acid (LCPUFA).

9. The method of claim 1, wherein the composition further comprises at least 5% by weight of omega-3 DPA.

10. The method of claim 1, wherein the composition comprises the very long chain polyunsaturated fatty acid (VLCPUFA) in the form of an ethyl ester, a triglyceride or a wax ester, and/or the composition further comprises at least one C20-22 long chain polyunsaturated fatty acid (LCPUFA) in the form of an ethyl ester, a triglyceride or a wax ester.

11. The method of claim 1, wherein the composition comprises at least one VLCPUFA selected from the group consisting of C26:7n3, C28:7n3, C28:8n3 and C24:1.

12. The method of claim 1, wherein the composition comprises C28:8n3 as a VLCPUFA.

13. The method of claim 1, wherein the treatment is for alleviation of symptoms of the Dry Eye Disease (DED) or the meibomianitis of the subject.

14. The method of claim 1, wherein the treatment has at least one effect selected from the group consisting of (1) to alleviate or relive ocular symptoms associated with the Dry Eye Disease (DED) or the meibomianitis; (2) to treat dry eye symptoms as a side-effect of a medication, radiation or conjunctivitis; (3) as a supplement for maintaining healthy eyes and preventing dry eye diseases and discomfort from developing as a person ages or is exposed to dry eye diseases because of environmental conditions, medication or a related health factor; and (4) to treat and alleviate dry eye discomfort linked to aging, menopause, hormone changes, allergies, dry environment, use of contact lenses, high computer use, or high television use.

15. The method of claim 1, wherein the composition is an ingredient in an oral pharmaceutical preparation.

16. The method of claim 1, wherein the composition is an ingredient in at least one pharmaceutical preparation selected from the group consisting of an eye drop, a spray, an ointment, a cream, a salve, a lotion, a gel, and an ocular mini tablet.

17. An ophthalmic formulation comprising a composition, wherein the composition comprises at least 5% by weight of a very long chain polyunsaturated fatty acid (VLCPUFA) having a chain length of more than 22 carbon atoms, wherein the VLCPUFA is derived from a natural oil selected from the group consisting of fish oil, squid oil, krill oil, copepod oil, and algal oil.

18. The formulation of claim 17, wherein the formulation is in the form of at least one form selected from the group consisting of an eye drop, a spray, an ointment, a cream, a salve, a lotion, a gel, and an ocular mini tablet.

19. The method of claim 3, wherein the composition comprises at least 20% by weight of the very long chain polyunsaturated fatty acid (VLCPUFA).

20. The method of claim 12, wherein the composition comprises at least 4% by weight of the C28:8n3.

21. The method of claim 14, wherein the treatment is to alleviate or relive ocular symptoms associated with palliative treatment and eye care or ophthalmic tissue.

* * * * *